United States Patent [19]

Dunnett et al.

[11] Patent Number: 5,401,759
[45] Date of Patent: Mar. 28, 1995

[54] NIMODIPINE ENHANCED GROWTH & VASCULARIZATION OF NEURAL GRAFTS

[75] Inventors: Stephen B. Dunnett, Linton, United Kingdom; Stanley Finger, St. Louis, Mo.

[73] Assignee: Miles Inc., Elkhart, Ind.

[21] Appl. No.: 892,738

[22] Filed: Jun. 3, 1992

Related U.S. Application Data

[63] Continuation of Ser. No. 731,346, Jul. 15, 1991, abandoned, which is a continuation of Ser. No. 437,534, Nov. 16, 1989, abandoned.

[51] Int. Cl.$^6$ ............................................. A61K 31/44
[52] U.S. Cl. ..................................................... 514/356
[58] Field of Search ......................................... 514/356

[56] References Cited

U.S. PATENT DOCUMENTS 4,406,906  9/1983  Meyer .................................. 424/263

OTHER PUBLICATIONS

Gisvold et al. "Drug Therapy In Brain Ischaemia" Br. J. Anaesth, (1985) 57, 96–109.

*Primary Examiner*—Zohren Fay

[57] ABSTRACT

The invention relates to a method of enhancing vascularization and growth of neural grafts in warm-blooded animals, especially man, comprising administering an effective amount of the nimodipine, a calcium channel blocker, having the formula 1,4-dihydro-2,6-dimethyl-4-(3'-nitrophenyl)-pyridine-3-($\beta$-methoxyethyl ester)-5-(isopropyl ester) to the animals to achieve such enhancement and growth. The method enhances the survival rate of transplantations.

10 Claims, 5 Drawing Sheets

NIMODIPINE ENHANCED GROWTH & VASCULARIZATION OF NEURAL GRAFTS

This application is a continuation of Ser. No. 07/731,346, filed on Jul. 15, 1991, which is, in turn, a continuation of Ser. No. 07/437,534, filed on Nov. 16, 1989, both now abandoned.

FIELD OF THE INVENTION

This invention relates to a method for increasing the survival and growth of neural transplants comprising administering an effective amount to enhance vascularization of the compound having the formula 1,4-dihydro-2,6-dimethyl-4-(3'-nitrophenyl)-pyridine-3-(β-methoxyethyl ester)-5-(isopropyl ester) hereinafter referred to as nimodipine.

BACKGROUND OF THE INVENTION

Unsymmetrical esters of 1,4-dihydropyridine-dicarboxylic acids, processes for their production and their use as coronary and antihypertensive agents are disclosed in U.S. Pat. No. 3,799,934. U.S. Pat. No. 3,932,645 includes the mixture of nimodipine and an inert carrier and the use of the compound to effect coronary vascular dilatation. Additionally, it has been found that nimodipine has an advantageous action on cerebral circulatory disturbances. U.S. Pat. No. 4,406,906 discloses a method of combating pathologically reduced cerebral functions and performance weaknesses, cerebral insufficiency and disorders in cerebral circulation and metabolism.

Nimodipine has been the subject of considerable investigation. Studies conducted by Harper et al, J. Cereb. Blood Flow Metab., 1: 49–356, 1981 indicated that nimodipine crosses the blood-brain barrier. The dilatory effects of nimodipine are known to be more selective to the cerebral vessels than hydralazine. Harris et al, Stroke 13: 759–766, 1982); Kazda and Towart, Acta Neurochirurgica, 63: 259–265, 1982; Towart et al, Arzneimittelforsch, 32: 338–346, 1982. Further, nimodipine exerts a cerebral vasodilatory effect without increasing intracranial pressure. Hadley et al, J. Neurosurg., 66: 387–393, 1987.

Under appropriate circumstances, embryonic CNS tissue readily survives transplantation into the adult brain (Azmitia, E. C. and A. Björklund, Eds. 1987, Cell and Tissue Transplantation into the Adult Brain, Ann. N.Y. Acad. Sci., 495; Björklund, A., and U. Stenevi, Eds. 1985, Neural Grafting in the Mammalian CNS, Elsevier, Amsterdam). The conditions for viable transplantation involve several factors, including the age and developmental status of the donor tissue and the suitability of the host transplantation site.

The optimal developmental status of the donor tissue appears to be related to the few days in embryonic development after the stage of final cell division of the particular group of neurons under investigation (Das, G. D., et al, 1980, Am. J. Anat. 158: 135–145; Olson, L., et al, 1983, Pages 407–442 in S. Federoff, Ed. Advances in Cellular Neurology, Vol. 4, Academic Press, New York; Seiger, A., 1985, Pages 71–77 in A. Björklund and U. Stenevi, Eds., Neural Grafting in the Mammalian CNS, Elsevier, Amsterdam). For mesencephalic dopamine cell suspension grafts in rats, the optimal age for transplantation is around Embryonic Day 14 (E14; crown-rump length, CRL, 11–14 mm), and by E16–E17 (CRL, 16–20 mm) only poor survival is obtained (Björklund, A., et al, Cell Tissue Res., 212: 39–45; Brundin, P., et al, 1988, Dev. Brain Res., 39: 233–243; Dunnett, S. B., et al, Brain Res., 415: 63–78). Moreover, graft survival is optimal when made within 1–3 hours of embryonic dissection, unless the cells to be transplanted are cryopreserved or maintained in culture (Brundin, P. et al, 1988, ibid; Das, G. D., et al, 1983, J. Neurosci., Methods 8: 1–15; Gage, F. H., et al 198, Neurosci. Lett., 60: 133–137). For example, Brundin et al, 1985, Brain Res., 331: 251–259, used vital cell stains to characterize the viability of graft cells in suspension and found that the viability of embryonic dopamine neurons declined dramatically 3–6 hours after dissection and preparation.

Another factor important for graft survival is the provision of a suitable transplantation site in the host brain with adequate vascularization to nurture the newly implanted tissue. This is particularly important for grafts of "solid" tissue pieces (Stenevi, U., et al, 1976, Brain Res., 114: 1–20), but has been thought to be less critical for suspension grafts. Thus, Lawrence et al (1984, Neuro-science, 12: 745–760) observed that fragile host blood vessels begin to grow into hippocampal grafts within 24 hours of transplantation, and within the first week considerable growth of both wide-diameter reactive vessels and dilated thin-walled marginal vessels gives rise to many small capillaries invading the transplant. Smith and Ebner (1986, The differentiation of non-neural elements in neocortical transplants, pages 81–101 in G. D. Das and R. B. Wallace, Eds., Neural Transplantation Research, Springer, N.Y.) and Rosenstein (1987, Science, 235: 772–774) also observed a substantial growth of blood vessels into neocortical transplants, but emphasized that the vessels appear to retain immature properties, such as relative permeability to circulating proteins. Rosenstein (ibid) hypothesized that an incomplete blood-brain barrier may serve to promote graft survival by permitting exposure of the fetal cells to blood-borne growth factors derived from the host brain.

Nimodipine, (isopropyl(2-methoxyethyl)14-dihydro-2,6-dimethyl-4-(3-nitrophenyl)-3,5-pyridine dicarboxylate) is a dihydropyridine which acts as a calcium channel antagonist (Betz, E., et al, Eds. 1985, Nimodipine: Pharmacological and Clinical Properties, Schattauer, Stuttgart; Harris, R. J., et al 1982, Stroke, 13: 759–766). This drug selectively dilates cerebral blood vessels and increases cerebral blood flow without a concomitant effect on systemic arterial pressure (Towart, R., et al, 1985, Effects of the calcium antagonist nimodipine on isolated cerebral vessels, pages 207–215; and Kazda, S., et al, 1985, Prevention of acute and chronic cerebrovascular damage with nimodipine in animal experiments, pages 31–43, both in E. Betz, K. Deck and F. Hoffmeister, Eds., Nimodipine: Pharmacological and Clinical Properties, Schattauer, Stuttgart). Nimodipine appears to be especially potent in areas with inadequate circulation (Harper, A. M., 1985, Effect of a dihydropyridine-type calcium antagonist of cerebral blood flow and metabolism, in A. Flechenstein, C. Van Breemen, R. Gross and F. Hoffmeister Eds., Cardiovascular Effect of Dihydropyridine-Type Calcium Antagonists and Agonists, Springer, Berlin; Mohamed, A. A., et al, 1985, The effect of nimodipine on local cerebral blood flow, glucose use and focal cerebral ischemia using acute autoradiographic techniques, pages 105–112 in E. Betz, K. Deck and F. Hoffmeister, Eds., Nimodipine: Pharmacological and Clinical Properties, Schattauer, Stuttgart). These properties of nimodipine have led to it being used clinically to enhance blood flow in migraine and cluster headaches and to treat certain types of ischemic brain insult (Dorn, M., 1985, Effect of nimodipine on the well-being, symptoms and efficiency of ambulatory patients with cerebrovascular disorders, pages 295–304; Held, K., et al, 1985, Efficacy and tolerability of nimodipine in patients with old-age cerebrovascular dysfunction, pages 289–292; Menazzi, D., et al, 1985, Nimodipine in the treatment of chronic cerebrovascular insufficiency, pages 329–331; and Mikus, P., et al, 1985, Nimodipine, a centrally active calcium antagonist, Results of a clinicopsychometric study, pages 329–331, all in E. Betz, K. Deck, and F. Hoffmeister, Eds., Nimodipine: Pharmacological and Clinical Properties, Schattauer, Stuttgart).

The present study was designed to test the hypothesis that nimodipine might also increase the viability of neural transplants by enhancing vascularization of the grafts. The results of this study were published by Finger and Dunnett in Experimental Neurology, 104, 1–9, 1989. Transplantation of embryonic ventral mesencephalic cells into the neostriatum of rats with unilateral dopamine-depleting lesions was chosen as the model system for investigation. The effects of nimodipine on the survival, growth, and vascularization of the grafts were considered, both under optimal transplantation conditions and using tissue considered suboptimal either by virtue of older donor age or by maintaining the cells for several hours at room temperature prior to transplantation.

DESCRIPTION OF THE DRAWINGS

FIG. 1 contains photomicrographs of blood vessels perfused with Indian ink in grafts and host brain. The sections are taken at the level of the maximum cross-sectional area of the grafts, counter-stained with cresyl violet, and viewed under both bright- and dark-field illumination. In the bright-and dark-field pairs (B/C, E/F, and H/J), the graft-host border can be determined from the bright-field illumination, and small arrows indicate the same blood vessels in both fields. (A) Location of a typical graft in the caudate putamen. This example was taken from an E14 graft of a nimodipine-treated rat. The box is shown at higher magnification in E and F. (B, C) An E14 graft from a vehicle-treated rat, viewed in bright-and dark-field, respectively. (D) E14 grafts from a nimodipine-treated rat. (E,F) A second E14 graft from a nimodipine-treated rat, viewed in bright- and dark-field, respectively. Note that the density of blood vessels in the grafts from nimodipine-treated rats (D, F) is higher than that in those from the vehicle-treated rats (C), although these grafts were all prepared from the same E14 cell suspension. (G) Gliotic track indicating site of injection of an E14/6 H graft in a vehicle-treated rat. Macrophages along the injection track are clearly seen under dark-field illumination. (H, J) Healthy E14/6 H graft in a nimodipine-treated rat, viewed under bright-and dark-field illumination, respectively. Abbreviations: cc, corpus callosum; cp, caudate putamen; g, graft. Scale bars: 1 mm in A, 250 μm in B, B–J all at same magnification.

FIG. 3 shows vascularization of the grafts. The animals of each graft group are shown in separate panels. Each panel shows scatter plots of capillary length in millimeters (ordinate) against maximum cross-sectional area of the graft for each animal treated with nimodipine (filled circles) or vehicle alone (open circles). The best-fit regression lines for the drug and vehicle conditions are shown as solid and dashed lines, respectively.

SUMMARY OF THE INVENTION

The invention provides a method of enhancing vascularization and growth of neural grafts in warm-blooded animals, especially man, comprising administering an effective amount of nimodipine to the animals to achieve such enhancement and growth. Nimodipine has the formula: 1,4-dihydro-2,6-dimethyl-4-(3'-nitrophenyl)-pyridine-3-(β-methoxyethyl ester)-5-(isopropyl ester).

DESCRIPTION OF THE INVENTION

Surprisingly, nimodipine used according to the present invention, enhances vascularization and growth of neural grafts, in doses administered over time. It is believed this neural enhancement will enhance recovery of function after brain damage and the survival of the transplant. The enhancement in neural grafts is seen without effect on normal tissue. Thereby it is believed that the function of damaged brain tissue can be improved without effect on normal brain tissue.

It is recognized that enhanced vascularization is a function of delivering an effective amount of nimodipine for a sufficient duration. It is within the scope of this invention that an effective amount of nimodipine may be delivered utilizing sustained release systems. Such sustained release systems are well known in the prior art, for example, U.S. Pat. No. 4,765,989 discloses an osmotic system for delivering drugs at a broad range of drug delivery rates and can deliver the drugs according to a predetermined drug release pattern over time.

The present invention finds application in all mammalian species, including both humans and animals.

The experiment demonstrates that treatment with the calcium channel antagonist, nimodipine, can influence the vascularization and growth of neural tissue grafts in the adult brain. The drug-induced increase in the capillary density and in the volume of the grafts was more marked under conditions where the transplanted tissue was suboptimal, in terms of either developmental stage or tissue freshness, than in the E14 short-delay grafts. This increased vascularization is believed to lead to enhanced survival of transplants and an increase in recovery of brain function.

In man, the method utilizes nimodipine in dosages, given orally or intraveneously, of from 20 mg per day to 80 mg four times per day in a course of treatment which is greater than six days and commonly at least fourteen days. Alternatively, or in addition to the treatment of the patient after the transplant operation, the vascularization and growth of neural tissue grafts may be enhanced by soaking or perfusing the tissue in nimodipine prior to transplant. This has the advantage of allowing higher dosages of nimodipine to be used, as high as 10.0 to 15.0 mg per kg tissue weight or greater, while minimizing the dosage given to the patient. It is believed that the latter method, in addition or in alternative to administration after transplant, increases the survival of the transplant and enhances the recovery of brain function.

It is well established that the developmental stage of the donor tissue is a primary factor influencing graft survival; embryonic cells only survive transplantation to the adult brain when taken during a particular time window of embryonic development (Björklund, A., and U. Stenevi, 1984, Ann. Rev. Neurosci. 7: 279–308; Das et al, 1980, ibid; and Olson et al, 1983, ibid). The critical time window varies for different populations of cells (Olson, et al, 1983, ibid; Seiger, 1985, ibid) and appears to relate to the stage at which final cell division has taken place but prior to extensive neurite outgrowth. For the dopamine cells of the substantia nigra, the critical stage appears to be between 13 and 16 days of gestational age of a rat (Björklund et al, 1980, ibid; Brundin et al, 1988, ibid; Seiger, 1985, ibid). For example, Brundin et al (1988, ibid) counted the number of dopamine fluorescent cells surviving in ventral mesencephalic grafts derived from 14-, 16-, and 20-day embryos and found very poor survival in the oldest donor group. In the present study, the comparable survival of grafts derived from similarly aged embryos, using a different measure of survival and growth, namely, graft volume, was confirmed.

The critical age for implanted tissue of between 13 and 16 days for a rate is believed to correspond with 6 to 9.5 week of gestation in human fetal development for good graft viability. The evidence for this is provided by systematic comparison of the viability of human fetal nigral cells transplanted to the rat brain once the rats have been immunosuppressed with cyclosporin to block immunological rejection of such xenografts. (Brudin P. et al., Exp. Brain Res., 65:235–240, (1986); Stromberg I. et al., Neuroscience Lett., 71:271–276, (1986); Clarke, D. J. et al., Exp. Brain Res., 73:115–126, 1988.) Some preliminary trials of human fetal nigral grafts in patients with Parkinson's disease have employed nigral tissues from 13 to 16 gestational week fetal donors (Madrazo I et al, 1988), somewhat older than the optimum predicted by the previously mentioned experiments. Older than optimal tissue was also used by Hitchcock et al, Lancet, i:1274, 1988.

It is believed that this tissue was chosen because of availability and ease of dissection. The data provided herein suggests that nimodipine can enhance survival of tissues when the donor is older than the optimal gestational age. The 13 to 16 day critical period in the rat for untreated grafts can be extended up to 20 days with nimodipine treatment. The equivalent time window in human fetal development is 6 to 9.5 weeks, and above this age only poor results can be expected with untreated tissue. Nimodipine may enhance the viability of human fetal tissue from donors older than 9.5 weeks. This may be important in the context of standard procedures for therapeutic abortions which will determine the availability of tissue for transplantation. Nimodipine may allow donor tissues to be taken (for non-biological reasons) from late gestational age donors and still be viable. In addition, current regulations on transplants appear to be moving toward requiring full separation between donor and recipient. This will require a consequent increase in the delay before donor tissue can be implanted, potentially of several hours. Nimodipine enhances the survival of donor tissues of optimal age when subjected to delays in implantation which would normally impair viability. In addition to instances where optimal graft tissue is not available, nimodipine may be expected to enhance the viability of even optimal sources and facilitate handling of donor tissues, by promoting the extent of graft vascularization.

Whereas the volume of the grafts declined as the age of the donor tissue increased, it is noteworthy that the density of vascularization was comparable across all donor ages. The more interesting hypothesis to account for this effect is that the younger donor tissue stimulates or permits more extensive ingrowth of blood vessels of the graft and consequently sustains greater cell survival and growth of the graft up to a particular asymptotic level. However, an equally plausible interpretation is that the cells from young embryos undergo more extensive cell division or reduced cell death following transplantation, resulting in increased graft volume, and attract a corresponding proportional increase in vascular ingrowth to sustain the grafts. It is likely that both factors play a role, in that graft survival and growth probably represent an interaction of the viability of donor cells and the extent of vascularization that is achieved (see below).

In support of the importance of vascularization as a second factor critical for the viability of embryonic grafts, it has been found that pieces of peripheral or embryonic central nervous system tissue survived well in the adult brain only when placed in natural or artificial cavities having direct contact with pial membranes (Rosenstein, J. M., et al 1978, Nature (London) 276: 83–85; Stenevi, U., et al, 1976, ibid; Svendgaard, N.-A. A., et al, 1975, Adv. Anat. Embryol. Cell Biol. 51: 1–77). This was taken to imply that neural grafts depend on rapid and efficient vascularization for survival and growth (Björklund & Stenevi, 1984, ibid). However, some studies have suggested that survival of intraparenchymal grafts may be possible under certain conditions. For example, although Rosenstein (1987, ibid) found excellent growth of cortical tissue placed in contact with the vessel-rich choroidal plexus and pia in the fourth ventricle, he also noted that grafts derived from the youngest embryos in the study could survive when implanted directly into the neocortex. Furthermore, other investigators have reported good survival of cores of fetal cells injected into the adult hippocampus, septum or neocortex (Lawrence, J. M., 1984, ibid: Raisman, G. et al Neuroscience 9: 783–801; and Smith et al, 1986, ibid). The degree of cell dispersal may be a critical factor affecting graft survival and growth in these studies. The observation that embryonic tissue grows well throughout the brain when implanted as a dissociated cell suspension (Schmidt, R. H., et al, 1983, Intracerebral grafting of dissociated CNS tissue suspensions, pages 323–357 in F. Seil, Ed., Nerve, Organ, and Tissue Regeneration: Research Perspectives. Academic Press, New York; Schmidt, R. H., et al, 1981, Brain Res. 218: 347–356), in which the cells of the graft achieve maximal contact with the microvasculature of the host parenchyma, is consistent with this position. The results of the present study show that the growth of suspension grafts can be correlated with vascularization, a finding consistent with the importance that vascularization appears to have for solid tissue transplants. Moreover, the experimental findings indicate that pharmacological intervention can enhance the degree of vascularization and subsequent growth of the grafts.

The observation that nimodipine can dilate blood vessels, especially in areas that have been damaged, is well known (Betz, E., et al, 1985, ibid). Less is known about the effect of this drug on the growth of blood vessels in healthy and damaged neural tissue. The present results show that nimodipine can significantly increase vascularization in cell suspension grafts, whereas the drug appeared to have no lasting effect on vascularization in intact tissue on the opposite side of the brain. It should be noted that drug administration ended 4 weeks prior to sacrifice, so that changes in measures of graft vascularization are unlikely to be an artifact of vasodilative effects of the drug.

Although the mechanism by which vascularization was enhanced in the grafts is not clear, a number of possibilities present themselves. First, nimodipine may stimulate existing vessels in nearby areas to grow into the graft. In this case, graft viability would be a direct function of blood vessel growth. Second, nimodipine may increase the probability of cell survival in the graft, perhaps by preventing excessive calcium uptake. The healthier cells would provide a stronger stimulus for secondary blood vessel growth. In this case, blood vessel growth would be an indirect consequence of another action of the drug. Third, nimodipine may reduce loss of existing blood vessels in the area of the graft, a region characterized by damage from the cannula and perhaps some displacement and compression from the graft. Fourth, nimodipine may promote the growth of embryonic blood vessels present in the implanted tissue itself and their subsequent connections with the host vascular system. These alternative possibilities are necessarily speculative, and it is difficult to determine the relative contribution of each. However, the fourth possibility seems unlikely when cell suspensions are used, as was the case here, although anastomosis of blood vessels from the graft and host could contribute to increased vascularization in solid tissue grafts (Lawrence et al, 1984, ibid). Additional ultrastructural, immunological, and protein transport studies of the blood vessels in the grafts may shed some light on the direct and indirect effects of nimodipine on patterns of vascularization and the ways in which the different mechanisms could interact.

Methamphetamine-induced rotation was employed in the present experiment to assess the initial lesions, to match the rats between graft groups, and to provide an index of behavioral recovery. Although a separate group of animals receiving lesions alone was not included in the present experiment (with or without nimodipine treatment), the 6-OHDA-induced asymmetry in this test has been shown to be stable (and in some cases to increase further) over at least 6 months in the absence of a viable dopaminergic graft (Dunnett, S. B., et al, 1983, Acta Physiol. Scand. (Suppl.) 522: 29-37; Dunnett et al, 1987, ibid). A reduction in rotation over 6 weeks following transplantation was only seen in the group of rats receiving ventral mesencephalic grafts derived from 14-day embryos. Even in this group, the degree of recovery was only moderate. However, it should be noted that each rat received only a single cell suspension deposit in order to facilitate histological assessment of the grafts. In contrast, previous studies that have reported more dramatic recovery from rotational asymmetries in rats given unilateral nigrostriatal lesions have generally employed two or more graft deposits in order to maximize the number of dopamine cells injected and the extent of terminal reinnervation of the denervated host brain (Björklund et al, 1983, ibid; Brundin et al, 1985 and 1988, ibid; Dunnett et al, 1983 and 1987, ibid; and Schmidt, et al, 1981, ibid).

In the present study, there were no detectable differential effects of nimodipine on behavioral recovery. This was the case even though the volumes of the grafts in the E17 rats treated with nimodipine overlapped those of the E14 grafts that were administered vehicle alone. This might suggest that the drug-induced enhancement of vascularization and growth in the grafts was associated with improved survival or division of nondopaminergic cells still undergoing mitosis, rather than of the dopaminergic cells that had already completed final cell division at the time of drug administration. Tyrosine hydroxylase immunocytochemistry was attempted on sections containing the grafts from the present series of animals, but the perfusion and sectioning procedures used were found to be incompatible with obtaining a good immunohistochemical reaction. Further studies, in which the brain tissue is prepared specifically for histochemical visualization of catecholamine neurons in the grafts, would provide a means of testing this hypothesis.

In conclusion, intragastric administration of the calcium channel antagonist, nimodipine, was found to enhance vascularization and growth of neural grafts. This was best seen under suboptimal grafting conditions, such as advanced developmental status of the donor tissue or delays in conducting the transplantation surgery. These findings may have relevance for neural transplantation in the clinic, where it may not always be possible to achieve optimal staging of donor tissue or where practical considerations may result in implantation delays.

The following example discloses preferred embodiments of the invention, but does not limit the applicability of the invention which is solely defined by the claims.

EXAMPLE

Subjects

Sixty-four young adult female rats of the Sprague-Dawley strain (OLAC, Bicester, Oxon., UK) were used as graft recipients. The rats weighed 170-190 grams (g) at the start of the experiment. They were housed in groups of eight rats per cage, under a natural light-dark cycle with food and water available ad libitum. Graft tissue was taken from embryos of the same outbred strain at E14, E17, and E20 days of gestation.

Surgery

Lesions

All rats initially received unilateral lesions of the right nigrostriatal bundle, under 0.3 mg/100 g equithesin anesthesia. 6-Hydroxydopamine HBr/8 $\mu$g free base weight in 4 $\mu$l 0.01% ascorbate, 0.9% saline) was injected over 4 minutes via a 30-gauge stainless steel cannula stereotaxically positioned in the posterior hypothalamus at the following coordinates: anterior (A), −4.4 mm behind bregma; lateral (L), 0.9 mm to the midline; vertical (V), 7.8 mm below dura, with the incisor bar set −2.3 mm below the interaural line. Three minutes were allowed for diffusion prior to retraction of the cannula.

Transplantation

Graft tissue was dissected from the ventral mesencephalon (containing developing dopamine cells of the substantia nigra and ventral tegmental area) from embryos of 14, 17 and 20 days of gestational age (see Table 1). In each case the grafts were prepared as dissociated cell suspensions; the tissue pieces were collected in glucose-saline, incubated for 30 minutes at 37° C. in 0.1% trypsin, washed, and mechanically dissociated, according to a standard protocol (Björklund, A., et al, 1983, Acta Physiol. Scand. (Suppl.) 522: 1–7). The vital cell stains ethidiumbromide and acridine orange were used to determine the concentration and viability of cells in aliquots taken from each suspension (Brundin et al, 1985, ibid; and Schmidt et al, 1983, ibid) at the start of transplantation surgery.

TABLE I

Characteristics of the Graft Groups

| Groups | Gestation age Embryonic (days) | size (mm) | Suspension age (min) | Cells per graft[a] | Viability (%)[a] |
|---|---|---|---|---|---|
| E14 | 14 | 14 | 15–67 | 800,000 | 81.0 |
| E17 | 17 | 17 | 10–73 | 702,000 | 32.3 |
| E20 | 20 | 30 | 10–85 | 745,000 | 19.1 |
| E14/6H | 14 | 13 | 307–377 | 1,161,000 | 30.4 |

[a]Determined by cell counting in a hemocytometer following vital staining of the suspensions with the dyes ethidium bromide and acridine orange (8,27).

The 48 rats with the more complete depletions (as assessed by rotation tests—see below) were divided into three matched group (n=16 rats each) 16–23 days after the 6-OHDA lesions to receive suspension grafts derived from the 14-, 17-, and 20-day embryos (designated groups E14, E17, and E20). Preparation of the graft tissue was completed within 1 hour of dissection of the first embryo, and transplantation surgery took place within 10–90 minutes of preparation of the graft suspension for these three groups of rats. The remaining 16 rats, which had the least complete lesions as assessed by rotation, comprised the fourth graft group and received suspension grafts from 14-day embryos, but with a 5.5-hour delay interposed between washing the tissue after trypsin incubation and mechanical dissociation of the cell suspension. Transplantation surgery in this group (designated group E14/6 H) thus commenced approximately 6 hours after completion of the embryonic dissection.

Each rat received a single 3-μl graft injected stereotaxically into the right neostriatum under equithesin anesthesia. The cell suspension was injected over 3 minutes through the 23-gauge needle of a 10- μl glass syringe mounted directly in the electrode carrier of the stereotaxic frame. The coordinates for the injection were A, 1.0 mm; L, 2.5 mm; V, 4.5 mm, with the incisor bar set at −2.3 mm. A further 2 minutes was allowed for diffusion prior to retraction of the needle.

Nimodipine Administration

Since nimodipine is insoluble, it was administered (as in most previous studies using chronic treatments) by intragastric intubation as a suspension. Once they get used to being handled, the rats readily accept the feeding tube and can be intubated rapidly and with a minimum of discomfort. Half the rats (n=8) from each graft group received daily intubations of 15 mg/kg nimodipine for 2 weeks, beginning on the morning after transplantation surgery. The drug was suspended (15 mg/ml) in 2% aqueous methyl cellulose solution and administered by intragastric injection through plastic neonatal feeding tubes (size 4FG; Portex, Hythe, Kent, UK). The other half of each group received equivalent control intubations of the vehicle solution alone. Within each graft group, the two subgroups (drug or vehicle) were matched on the basis of their initial rotation scores (see below).

Rotation

Methamphetamine-induced rotation was tested in a bank of eight automated rotometer bowls modeled after the design of Ungerstedt and Arbuthnott (1970, Brain Res. 24: 485–493). Total 360° turns in the left and right directions were recorded over 90 minutes following ip injection of 5 mg/kg methamphetamine HCl. All rats were tested for methamphetamine-induced rotation 11 days after the initial lesion (prior to transplantation), and the net ipsilateral rates of rotation provided the basis for allocating the rats to matched groups (see above). The rats received a second test 40 days after transplantation surgery in order to assess any functional compensation attributable to the grafts.

Histology

All rats were sacrificed under deep barbiturate anesthesia 2 days after the second rotation test. They were perfused via the ascending aorta with 50–100 ml isotonic saline followed by 200–300 ml of a fixative containing 1 part Indian ink to 4 parts 10% formalin. The brains were then removed from the skull and stored 2–6 weeks in 10% formalin until sectioning. Frozen coronal sections were cut at 40 μm on a sledge microtome, and every sixth section was mounted on glass and lightly stained with cresyl violet.

Sections were studied under both bright- and darkfield illumination with a Leitz Dialux microscope with a drawing tube attachment. Tracings and measurements were conducted blind to the drug treatment of the individual animals. Three analyses were conducted on the histological sections.

First, the outline of the graft was traced at X25 magnification in successive sections. A graphics tablet (Grafpad, British Micro, Watford, Mddx., UK) was used to calculate the cross section areas, and the volume (V) of the grafts was estimated based on these areas and the section intervals (SI, i.e., 6×40 μm) according to the formula $$V = \Sigma(\text{area}) \times SI.$$

Second, the extent of vascularization within each graft was estimated in the section in which the graft achieved maximum cross section area. The ink-stained capillaries were traced at X63 magnification and total capillary length within the border of the graft was measured on graph paper.

Third, the extent of vascularization in intact tissue was similarly estimated by tracing and measuring the capillary network at X63 magnification in a randomly selected 0.125-mm$^2$ area (determined with a graticule in the eyepiece) in the left neostriatum of each animal, contralateral to the section containing the maximal cross section area of the graft.

Results

Body weight gain was equivalent for the rats given nimodipine and vehicle over the course of the experiment, and there was no indication that the drug affected the health of the rats in any way. However, seven rats were excluded from various analyses because either they died in response to the amphetamine injections or they failed to perfuse adequately.

Graft Survival

Figure 1A:
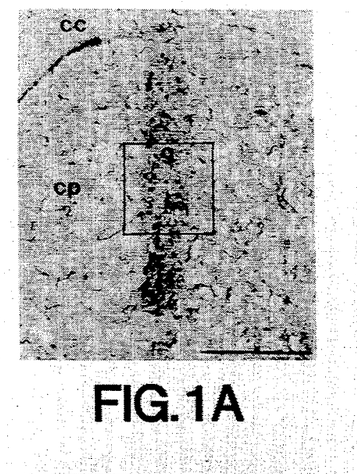
Figure 1B:
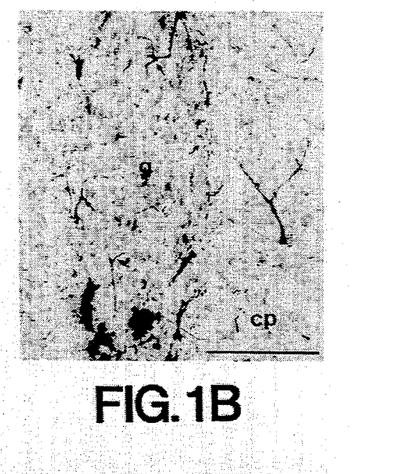
Figure 1C:
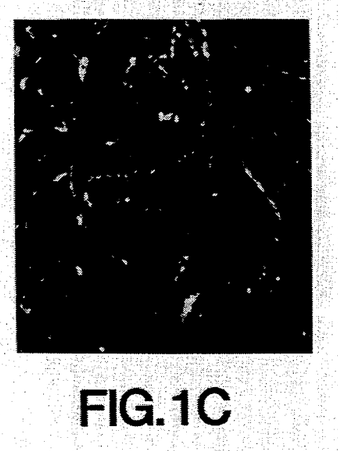
Figure 1D:
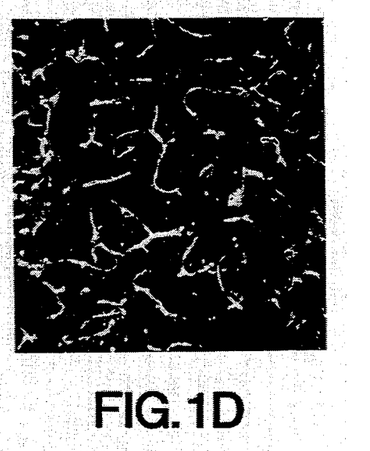
Figure 1E:
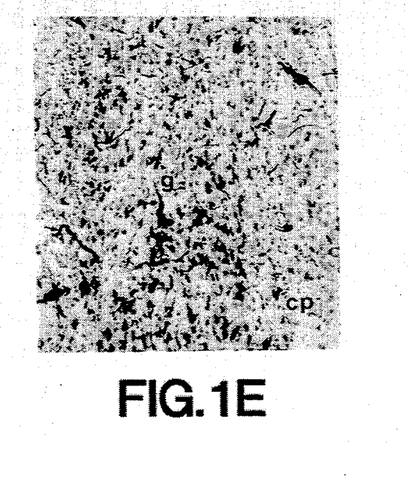
Figure 1F:
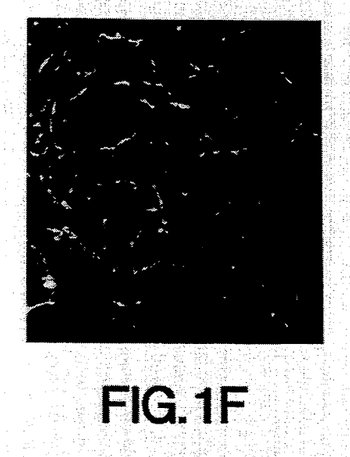
Figure 1G:
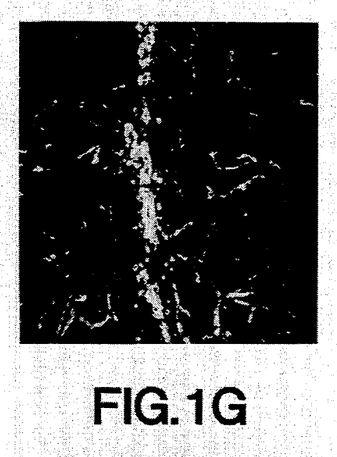
Figure 1H:
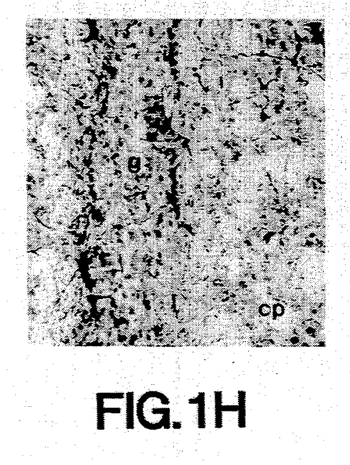
Figure 1J:
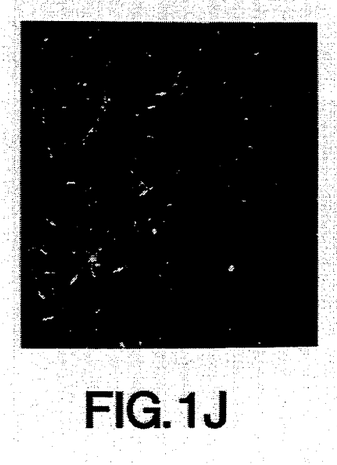

The grafts could be clearly distinguished from host parenchyma in the nissl-stained sections (see FIGS. 1A, 1B, 1E, and 1H). Surviving grafts were found in all E14, E17, and E14/6 H rats. In contrast, surviving graft cells could be detected in only two of seven vehicle rats and six of eight nimodipine-treated rats in the E20 group (Fisher's exact probability, P=0.100, ns). The injection track could be identified in all cases by an accumulation of macrophages that were most easily detected under darkfield illumination (see FIG. 1G), even in the absence of detectable surviving neurons in the grafts.

Graft Volume

Figure 2:
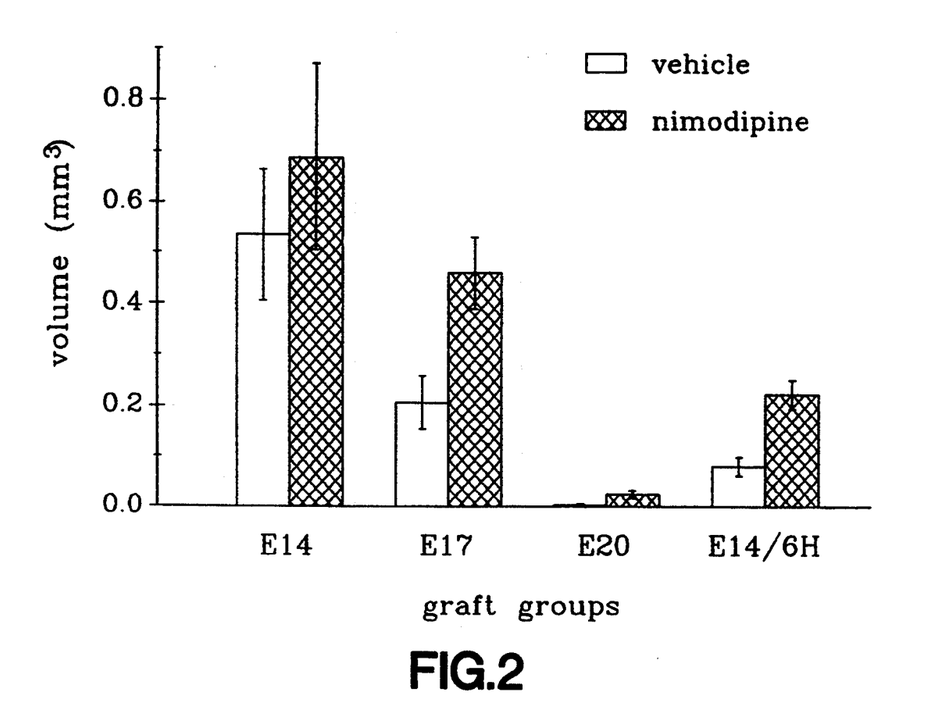
FIG. 2 shows the mean volume (ordinate) of the grafts in the four experimental groups of rats (abscissa) treated with nimodipine (hatched) or vehicle alone. Vertical bars indicate SEMs.
Figure 3A:
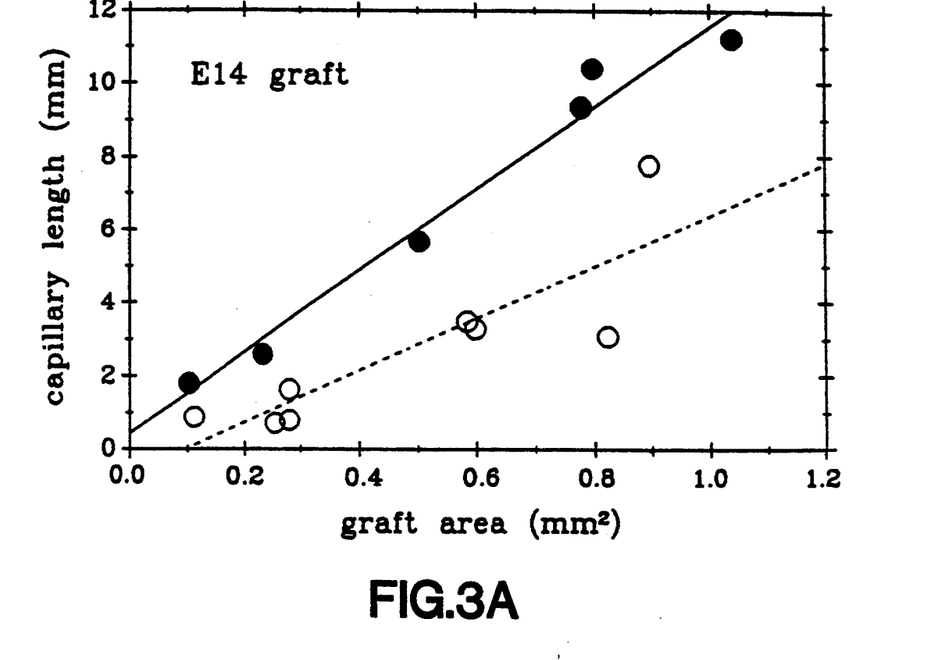
Figure 3B:
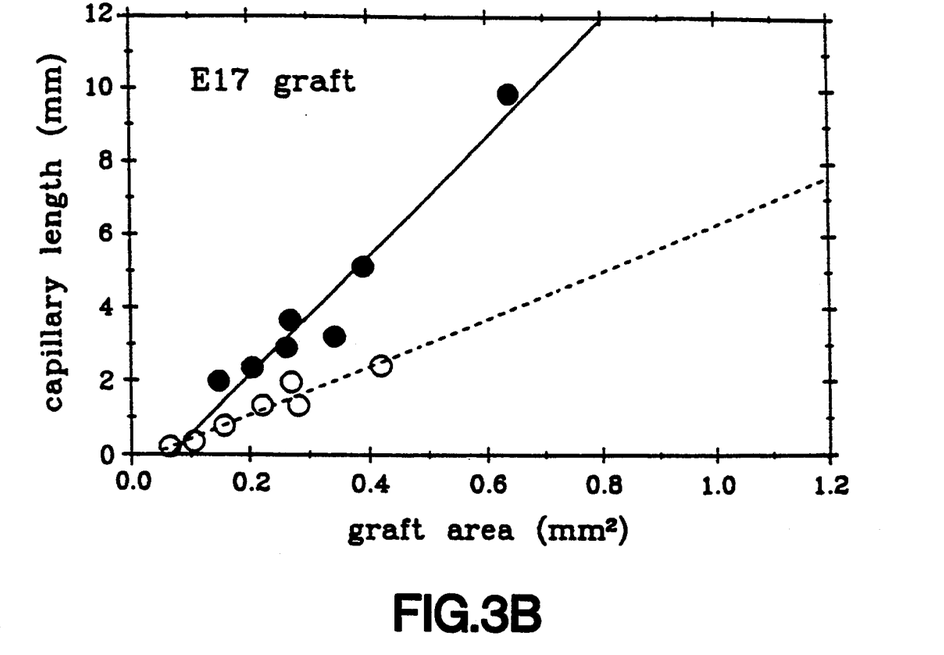
Figure 3C:
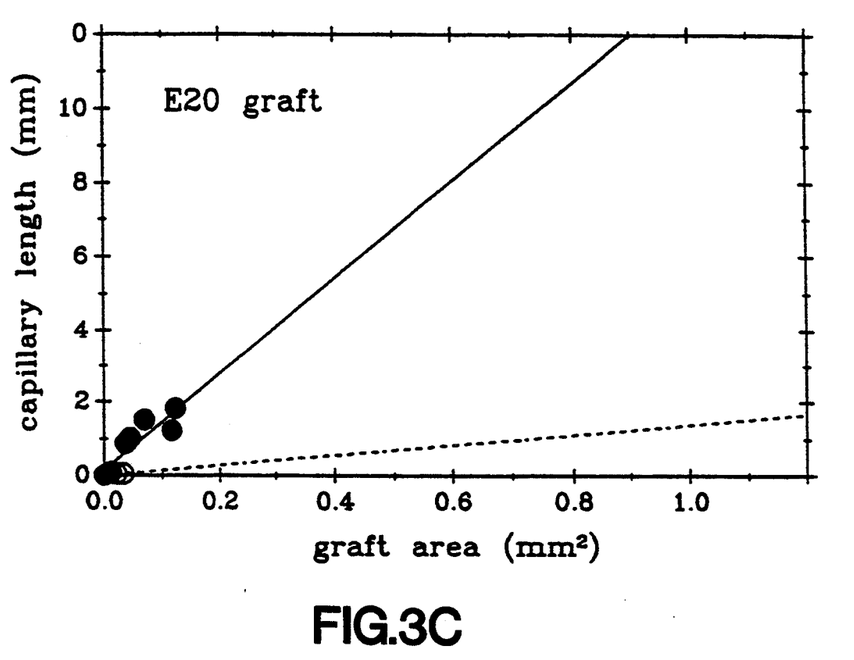
Figure 3D:
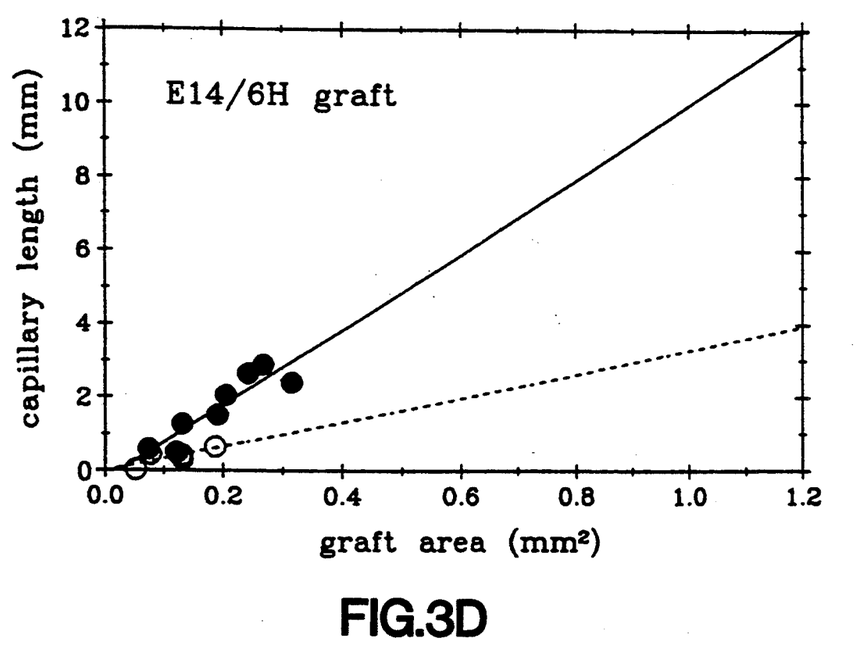

The volume of the grafts in the four graft groups, with and without nimodipine treatment, is shown in FIG. 2. A completely randomized analysis of variance with two factors (Donor Age and Drug) was conducted on the three groups which were matched on the initial rotation test (i.e., the E14, E17, and E20 rats). The analysis revealed that growth in volume of the grafts decreased as donor age increased (main effect of Donor Age, $F(2,39)=51.29$, $P<0.001$) and that whereas nimodipine fell short of having a significant effect on the vigorous growth of grafts in the E14 group it significantly enhanced the volume of graft tissue from the E17 and E20 donors (Drug X Donor Age interaction, $F(2,39)=3.28$, $P<0.05$). The data from group E14/6 H were analyzed separately from the other three groups, since these animals were not matched, but rather had a less complete lesion based on the initial rotation test. In the E14/6 H group also, nimodipine treatment significantly enhanced growth of tissue grafted after a 6-hour delay in suspension (Drug effect in the E14/6 H group, Student's $t(13)=4.14, P<0.001$).

Graft Vascularization

The vascularizations in the grafts and host brain were most easily observed under dark-field illumination (see FIGS. 1C, 1D, 1F, and 1J). Scatter diagrams for capillary length (CL, in mm) plotted against maximal cross-sectional area of each graft (CA, in mm$^2$) are shown in FIG. 3. The density of vascularization of the grafts in each group is provided by the slope of each regession lines (capillary length per unit area). The density of vascularization was relatively consistent within each group and drug treatment, as can be seen from the high positive correlations between CL and CA for the individual grafts in each subgroup (r=0.75–0.98; see Table 2), and which is shown schematically by the close fit of the regression lines in FIG. 3. Moreover, the individual data points for vascularization density (CL:CA) of the nimodipine-treated rats consistently fell above those for the saline-treated rats in all four groups (see FIG. 3), and the slopes of the regression lines were greater for the nimodipine-treated rats (see FIG. 3 and Table 2). The drug-induced increase in regression slope approached significance in the E14 group ($t(12)-1.76$, $P<0.1$) and was highly significant in all other graft groups (all $P<0.001$; see Table 2).

TABLE II

Density of Graft Vascularization in Each Treatment Group

| Groups | n | Treatment | r$^a$ | Slope | t$^b$ |
|---|---|---|---|---|---|
| E14 | 7 | Vehicle | 0.864 | 7.066 | |
| | 6 | Nimodipine | 0.987 | 11.124 | 1.757 |
| E17 | 7 | Vehicle | 0.963 | 6.543 | |
| | 7 | Nimodipine | 0.970 | 16.281 | 7.349* |
| E20 | 7 | Vehicle | 0.967 | 1.386 | |
| | 8 | Nimodipine | 0.905 | 13.158 | 6.312* |
| E14/6H | 7 | Vehicle | 0.753 | 3.287 | |
| | 8 | Nimodipine | 0.907 | 10.191 | 5.959* |

$^a$Correlation coefficient relating total capillary length to maximal cross-sectional area of the grafts within each group.
$^b$Student's t statistic comparing the regression slopes in the vehicle-treated and nimodipine-treated subgroups.
*P < 0.001.

The density of vascularization in the intact neostriatum did not differ between nimodipine-treated and vehicle rats (means, 18.09 and 18.07 mm/mm$^2$; effect of Drug, $F(1,50)=0.00$; Group X Drug interaction, $F(3,50)=0.71$; both ns), suggesting that the drug did not have lasting effects on the vascular anatomy of undamaged tissue.

Rotation

Figure 4:
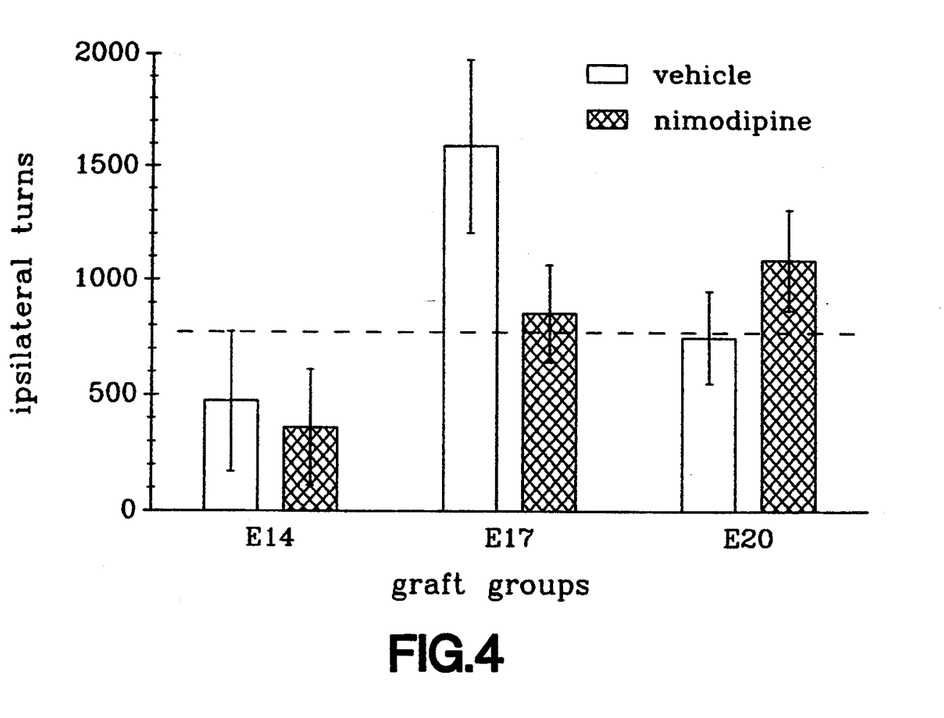
FIG. 4 shows rotation scores 6 weeks after transplantation for the three graft groups (abscissa) treated with nimodipine (hatched) or vehicle. The scores represent the mean net (ipsilateral-contralateral) 360° turns recorded over 90 minutes following injection of 5 mg/kg methamphetamine (ordinate). Vertical bars indicate SEMs. These groups were matched for rotation prior to transplantation and mean pregraft test scores are shown by the dashed lines. The E14/6 H group comprised rats that did not show strong rotation biases on the pregraft test and consequently was not included in this analysis.

On the initial rotation test (after the lesions but prior to transplantation), which was used to match the E14, E17, and E20 groups, the rats showed a mean net score of 771±68 ipsilateral turns (horizontal line in FIG. 4). Scores of these three groups of rats 6 weeks after transplantation are shown in FIG. 4. Analysis of variance revealed a significant main effect of Group ($F(2,37)-3.44$, $P<0.05$), due to the E14 rats turning less than the E17 and E20 rats. The E14 group was the only one in which the rotation scores fell below pretransplantation levels ($t(15)=1.88$, $P<0.05$), whereas the increased turning in the other two groups reached significance in the case of the E17 group ($t(15)-2.42$, $P<0.05$). Nimodipine treatment did not significantly affect rotation scores (Drug, $F(1,37)=0.11$, ns; Group X Drug, $F(2,37)-1.48$, ns), and so further analysis of the apparently greater turning in the vehicle-treated subgroup of the E17 group than in the nimodipine-treated subgroup is not appropriate. Further analysis of the 6-week rotation scores taking the pregraft scores as a covariate yielded equivalent results. Because all rats in the E14/6 H group had low turning scores (<50 turns in 90 min) on the initial rotation test and could not be equated with the rats in the other groups, their scores were excluded from these analyses.

It should be understood that many modifications and variations can be made in the proportions and components used herein without departing from the spirit and scope of the invention, which is solely defined by the claims.

What is claimed is:

1. A method of enhancing vascularization and growth of neural grafts in a warm-blooded animal comprising administering an effective amount of nimodipine to said animal to achieve such enhancement and growth.

2. The method of claim 1 wherein nimodipine has the formula: 1,4-dihydro-2,6-dimethyl-4-(3'-nitrophenyl)-pyridine-3-($\beta$-methoxyethyl ester)-5-(isopropyl ester).

3. The method of claim 2 in which the active compound is administered to deliver an effective amount of about 0.1 to 5.0 milligrams per kilogram body weight per day for greater than six days.

4. The method of claim 3 wherein the effective amount is about 5.0 milligrams per kilogram body weight per day which is administered for at least fourteen (14) days.

5. The method of claim 4 in which an oral dosage of from about 20 milligrams to about 80 milligrams is administered, four times per day.

6. A method of enhancing vascularization and growth of neural grafts in a warm-blooded animal comprising soaking or perfusing neural graft tissue in an effective amount of nimodipine having the formula 1,4-dihydro-2,6-dimethyl-4-(3'-nitrophenyl)-pyridine-3-(β-methoxyethyl ester)-5-(isopropyl ester) prior to transplantation.

7. The method of claim 6 in which the effective amount of nimodipine is from about 10.0 to about 15.0 milligrams per kilogram of tissue.

8. A method of enhancing the viability of neural graft tissue, comprising soaking or perfusing neural graft tissue in an effective amount of nimodipine having the formula 1,4-dihydro-2,6-dimethyl-4-(3'-nitrophenyl-pyridine-3-(β-methoxyethyl ester)-5-(isopropyl ester) prior to transplantation.

9. The method of claim 1 in which the warm-blooded animal is man.

10. The method of claim 6 in which the warm-blooded animal is man.

* * * * *